United States Patent [19]

Snyder

[11] 4,299,813

[45] Nov. 10, 1981

[54] ASSAY KIT AND METHOD

[76] Inventor: Solomon H. Snyder, 2300 W. Rogers Ave., Baltimore, Md. 21209

[21] Appl. No.: 40,292

[22] Filed: May 17, 1979

[51] Int. Cl.³ .................. G01N 33/48; G01T 1/00; B65D 71/00
[52] U.S. Cl. ................... 424/1; 23/230 B; 422/61; 424/12
[58] Field of Search ............ 424/1, 1.5, 12; 422/61; 23/230 B

[56] References Cited

U.S. PATENT DOCUMENTS 4,197,288   4/1980   Snyder ........................ 424/1

Primary Examiner—Benjamin R. Padgett
Assistant Examiner—Christine M. Nucker
Attorney, Agent, or Firm—Donald Brown

[57] ABSTRACT

Method and kit for determining levels of tricyclic antidepressants in body fluid, the method including the step of measuring inhibition of the binding of radioactive muscarinic cholinergic or radioactive histamine $H_1$ receptor binder to muscarinic cholinergic or histamine $H_1$ receptor material caused by tricyclic antidepressant present in the body fluid.

34 Claims, 3 Drawing Figures

ASSAY KIT AND METHOD

BACKGROUND OF THE DISCLOSURE

Tricyclic antidepressants are among the most important drugs in clinical psychiatry. (See the Physicians Desk Reference, 32 Edition, 1978, for disclosure of those tricyclic antidepressants which are in clinical use). The dosage requirements vary considerably among patients. Moreover, numerous published studies have indicated that on identical doses the plasma levels of these drugs can vary 30 fold or more in different patients. Attaining the optimal dose is important in securing maximal therapeutic benefit with minimal side effects. Serious cardiac side effects as well as anticholinergic effects such as dry mouth, difficulty urinating, and interference with eye pressure which could precipitate glaucoma are among the side effects to be avoided. Studies which have measured blood levels by a variety of techniques, most frequently gas chromatography, have indicated that patients show poor therapeutic responses with blood levels which are below the optimal range. See the publications: Ziegler, V. E., et al Arch. Gen. Psychiat. 34:607, 1977; Glassman, A. H., et al. Arch. Gen. Psychiat. 34:197, 1977: Gram, L. F., et al Clin. Pharmacol. Ther. 19:318, 1975; Asberg, M., Clin. Pharmacol. Ther. 16:215, 1974.

Most of the techniques available for tricyclic antidepressants cannot be used readily in routine hospital laboratories. It is generally felt that a simple and sensitive technique to measure these drugs in blood and other body tissues would facilitate the selection of optimal doses.

Presently available techniques are usually only applicable to single drugs. Ideally one would like a technique which can be used with all of the agents.

Clinically employed tricyclic antidepressant drugs have considerable potency in blocking muscarinic cholinergic receptors. See the publication: Snyder, S. H. and Yamamura, H. I. Arch. Gen. Psychiat. 34:236, 1977. Most of these drugs also have considerable potency in blocking histamine $H_1$ receptors. See the publication: Tran, V. T., Chang, R. S. L. and Snyder, S. H., Proc. Natl. Acad. Sci. USA, 75:6290 1978. The information contained in these above mentioned publications does not provide a tool for measuring amounts of tricyclic antidepressants in body fluids of human patients, because a number of needed elements, all of which were yet to be discovered, had to be discovered to exist for a successful assay for levels of tricyclic antidepressants. It was also necessary to discover the nonspecific effects of body fluids on the binding properties of the muscarinic cholinergic and histamine $H_1$ receptors and discover means of reducing or abolishing them. It was also necessary to discover that tricyclic antidepressants added to body fluids could be recovered in a form that would still interact with muscarinic cholinergic and histamine $H_1$ receptors. It was also necessary to show that in the presence of body fluids increasing amounts of tricyclic antidepressants would in a predictable fashion produce a greater blockade of muscarinic cholinergic and histamine $H_1$ receptors. Only after making a series of discoveries as disclosed herein which reduced nonspecific effects of body fluids on the muscarinic cholinergic and histamine $H_1$ receptors, permitting recovery of added tricyclic depressant drugs and resulting in reproducible augmentations in receptor blockage with increasing amounts of tricyclic antidepressants in body fluids was it possible to measure tricyclic antidepressants in body fluids with this invention.

BRIEF DESCRIPTION OF THE DISCLOSURE

The present invention is directed to a new technique which permits rapid determination of the concentration of tricyclic antidepressants as well as any active metabolites thereof in patient's body fluids. The making of this determination is important in order to obtain the desired medicinal effects of these drugs. While the desirable concentration of tricyclic antidepressant drugs in the patient's blood or other bodily fluid is known, it had been found that the uptake of these drugs by most patients is variable so that one has no assurance that a certain dose of tricyclic antidepressant administered to the patient will produce the desired concentration in the blood. The prior art techniques for measuring concentrations of tricyclic antidepressants, as mentioned previously, are not applicable to all available tricyclic antidepressants. Accordingly, a new and improved technique that could easily and rapidly be used was necessary to ensure that patients were being properly dosed to achieve beneficial effects without causing harmful side effects.

The present invention provides such a technique and is based on the fact that tricyclic antidepressants will successfully compete with the binding of radioactive receptor binders to muscarinic cholinergic receptors and/or histamine $H_1$ receptors in such a manner that an accurate determination of tricyclic antidepressant concentration in body fluids can readily be determined.

The present invention is also based in part upon the discovery that once the competition of radioactive drug to the muscarinic cholinergic receptors or histamine $H_1$ receptors has proceeded for the desired time, radioactive labeled receptor binder attached to receptor material can be successfully separated from free drug binder and receptor material and bodily fluids without destroying the accuracy of the concentration measurement to be made.

After the separation, the level of radioactive binder used to label the muscarinic cholinergic receptors or histamine $H_1$ receptors can be measured in a conventional radioactive measurement device, e.g. scintillation counter or gamma counter, depending on the radionuclide of the radioactive binder employed to label the receptor and compared with standard curves to determine the concentration of the tricyclic antidepressant in the patient. Normally a radioactive labeled drug will be used as the binder, however any radioactive labeled binder may be used so long as it will compete for the receptor with the drug to be measured.

Thus, there is described herein a method for measuring levels of tricyclic antidepressants (including any active metabolite thereof formed by the patient) in mammals, e.g. humans, based on the ability of these drugs to compete with the binding of radioactive receptor binders which label muscarinic cholinergic receptors and histamine $H_1$ receptors (ligands) to muscarinic cholinergic receptors and histamine $H_1$ receptors in appropriate tissues.

In this procedure increasing amounts of tricyclic antidepressant drugs decrease the binding of the radioactive labeled binder to muscarinic cholinergic or histamine $H_1$ receptor material. The biological fluid sample may be assayed without separation of the tricyclic antidepressant drug therefore, e.g. blood serum or blood plasma may be directly assayed to determine the levels of the tricyclic antidepressant drug. Alternatively the drugs may be extracted from the tissue and the tricyclic antidepressant and one of its metabolites separated so that they may be separately determined.

Suitable muscarinic cholinergic or histamine $H_1$ receptor material is obtained from animal tissues enriched in these receptors such as the brain, lung, heart, or any type of cultured cell containing the receptors. Suitable muscarinic cholinergic or histamine $H_1$ receptor material is obtained from humans or from a variety of animal species including cows, rats, or birds.

The muscarinic cholinergic or histamine $H_1$ receptor material may be used as such or fractionated in a conventional manner to obtain fractions enriched in receptor-containing membranes and may be washed or unwashed.

The muscarinic cholinergic or histamine $H_1$ receptor material may preferably be sold as a conventional freeze dried preparation in a test tube, e.g. coupled to the interior of the test tube, so that the binder and drug may be easily added to it.

As the radioactive muscarinic cholinergic receptor binder, radioactive labeled compounds such as $^3H$-quinuclidinyl benzilate, $^{125}I$-quinuclidinyl benzilate, $^{125}I$-propylbenzilyl choline mustard or any other analogues of drugs which are antagonists or agonists of the muscarinic cholinergic receptor having binding properties at the muscarinic cholinergic receptor may be employed. As the histamine $H_1$ receptor binder, $^3H$-mepyramine or any suitable antagonist or agonist at histamine $H_1$ receptors labeled with an appropriate radioactive label and which binds to histamine $H_1$ receptor may be employed.

In principal, these compounds are conventionally labeled in the manner well known in the prior art with any radionuclide. A listing of the radionuclides which are now conventionally in use in reagents and which may be used in this invention are listed in the index of radionuclides found on page 81 of the 1978 edition of the catalog of the New England Nuclear Corporation, Boston, Mass., U.S.A. (New England Nuclear, 1977). Among radionuclides which are preferred in this invention, the following may be mentioned: hydrogen-3 (tritium) and the radio isotopes of iodine ($^{123}I$, $^{124}I$, $^{125}I$, $^{126}I$, $^{128}I$, $^{130}I$, $^{131}I$, and $^{132}I$) with $^{125}I$ and $^{131}I$ being preferred from considerations of availability, half life and specific activity and the ability of radioactive iodine compounds to be readily counted using a conventional gamma counter usually available in hospitals and sold by Packard Instruments or others.

In a typical experiment, the membranes (muscarinic cholinergic receptor or histamine $H_1$ receptor material) can be incubated at various temperatures for various periods of time with appropriate ligand (muscarinic cholinergic or histamine $H_1$ receptor binder). Typically $^3H$-quinuclidinyl benzilate or $^3H$-mepyramine of high specific radioactivity purchased from New England Nuclear of Boston, Mass. is incubated with rat brain membranes with a buffer solution preferably at a pH of 7.7 at a temperature of 37° C. for 30 min and then filtered under vacuum through Whatman GF/B filters with two 5 ml rinses of cold buffer. The filters can be counted in liquid scintillation counters, e.g. Packard Instrument Scintillation Spectrometer model 3385. Counting may also be accomplished using a gamma counter.

Specific binding to the muscarinic cholinergic receptor is determined as the excess over blanks taken in the presence of 1 $\mu M$ oxotremorine or 0.01 $\mu M$ quinuclidinyl benzilate though blank values can be obtained using a variety of other agents that bind to the muscarinic cholinergic receptor. Specific binding to the histamine $H_1$ receptor is determined as the excess over blanks taken in the presence of 1 $\mu M$ triprolidine, a potent histamine $H_1$ receptor antagonist, or 100 $\mu M$ histamine, though blank values may be obtained using a variety of other agents that bind to the histamine $H_1$ receptor. In measuring competition for binding to the muscarinic cholinergic receptor, the ligand can be any muscarinic cholinergic agonist or antagonist or mixed agonist-antagonist labeled with radioactivity. For studies of drug competition at histamine $H_1$ receptors the ligand can be any histamine $H_1$ agonist or antagonist or mixed agonist-antagonist labeled with radioactivity.

Biological fluid samples, e.g. urine, blood plasma, blood serum, etc. supposedly containing tricyclic antidepressants are added to this assay. The biological samples can be added without any purification or may be subjected to purification procedures. Purification or concentration of the biological fluid containing the tricyclic antidepressant drugs can employ any of numerous chemical techniques including solvent extraction, column chromatography, adsorption onto specially treated fibers or other chemical substance or by any other chemical procedure which may help purify the tricyclic antidepressant drugs or concentrate it.

Some tricyclic antidepressants are tertiary amines, e.g. amitriptyline and imipramine which are converted in the body to corresponding secondary amines which in the case of amitriptyline would be nortriptyline and in the case of imipramine would be desmethylimipramine. Since the potencies of the secondary amines may differ from the potencies of the tertiary amine in competing for binding at muscarinic cholinergic or histamine $H_1$ receptors, it is desirable to separate the tertiary from the secondary amine prior to the assay. In blood samples from patients treated with tertiary amine tricyclic antidepressant drugs, levels of the secondary amine product are similar to levels of the tertiary amine. Accordingly, in this procedure tertiary amine tricyclic antidepressants may be separated from the secondary amine products prior to assay by a variety of techniques. These include extraction into organic solvent, ionic exchange chromatography, separation on a variety of filter papers and any other means which will separate the two types of drugs.

The amount of tricyclic antidepressant drug is quantified by the extent to which it decreases the binding of the labeled ligand to the muscarinic cholinergic receptor or histamine $H_1$ receptor. The values can be quantified in any convenient units. The incubation mixture for the receptor binding can include any of numerous additives to facilitate binding or to protect the drugs or labeled ligands. The duration of the incubation and its temperature can vary and involve any convenient period, though it is usually best to conduct the incubation to equilibrium, e.g. suitable time for incubation could be anywhere from 2 min to 4 hrs with 30 minutes being preferred. Receptor bound ligand can be trapped by filtration, centrifugation or any other known techniques which separate bound from unbound ligands.

It should also be understood that other suitable trapping techniques may also be used so long as they will permit the retention of the large sized muscarinic cholinergic or histamine $H_1$ receptor material having bound radioactive binder and tricyclic antidepressant drug while being able to separate the unbound radioactive binder (ligand) and free tricyclic antidepressant drugs. Other examples of suitable filter material include Millipore filters of various sizes, e.g. 0.6 micron diameter holes.

Preferably the muscarinic cholinergic or histamine $H_1$ receptor material is buffered by a buffering solution such as Tris-HCl buffer sold by Sigma Labs, St. Louis, Mo., having a pH of 7.7. Other suitable buffering solutions include sodium phosphate buffer, glycine buffer and Hepes buffer and others which will provide the preferred pH (6–9) in the mixture to permit rapid binding of the radioactive labeled binder to the muscarinic cholinergic or histamine $H_1$ receptor material.

Thus this invention provides a new and improved method for determining concentration in humans of tricyclic antidepressant drugs such as amitriptyline, imipramine, nortriptyline, desmethylimipramine, doxepin or protriptyline and others which are known in the art as therapeutically effective tricyclic antidepressants and which can compete for muscarinic cholinergic or histamine $H_1$ receptors.

In particular the method is easily practiced by preparing a mixture of radioactive binder, body fluid, e.g. blood serum, blood plasma or urine and muscarinic cholinergic or histamine $H_1$ receptor material, measuring the radioactivity, (counts) of the binder attached to the muscarinic cholinergic or histamine $H_1$ receptor material preferably after separating unbound materials (e.g. blood serum or plasma, binder, drug if present etc.) from the muscarinic cholinergic or histamine $H_1$ receptor material and then deriving the concentration of the tricyclic antidepressant drug from the standard curve which indicates the concentration of tricyclic antidepressant drug versus inhibition of the radioactive binder binding to the muscarinic cholinergic or histamine $H_1$ receptor material caused by the tricyclic antidepressant drug in the blood serum or plasma.

It has been discovered that the concentrations of bodily fluids such as blood plasma or blood serum in the assay are most preferably no greater than about 10% of the total assay volume of ingredients in the test tube. Concentrations of plasma or serum in excess of about 10% inhibit markedly binding of $^3H$-ligands to the muscarinic cholinergic and histamine $H_1$ receptor even without any drug present. Optimally, the concentration values should be less than 10%. Concentrations in excess of 10% may affect the validity of the assay test results. In this method the amount of body fluid is preferably greater than one microliter to assure consistently good results. When the drugs are purified by a procedure which separates them from plasma proteins which would interfere with the assay, then greater volumes of the drugs can be employed. One procedure which may usefully separate the drug from plasma protein is dialysis through any conventional membrane filter. Any other procedure which would separate the tricyclic antidepressant drugs from plasma proteins would be suitable. As used herein the total assay volume ingredients means the sum of ingredients in the test tube and the like prior to washing and adding scintillation fluid.

In addition, this invention provides a new composition of matter concerning radioactive binder, a tricyclic antidepressant drug and muscarinic cholinergic or histamine $H_1$ receptor material and blood serum or plasma and a kit as a mercantile unit comprising at least one container containing the following ingredients: muscarinic cholinergic receptor material or histamine $H_1$ receptor material, radioactive receptor binder for these receptor materials, and a standard amount of nonradioactive receptor binder. Each of these ingredients may also be packaged in one or more individual containers.

EXAMPLE I

Example I illustrates measurement of blood serum antidepressant levels using a histamine $H_1$ radioreceptor assay.

Materials and Methods

I. Buffer: 50 mM sodium phosphate buffer pH 7.4.

II. Histamine $H_1$ receptor material: Guinea pig cerebellar membranes were used on a source of receptor. Male guinea pigs weighing 350 g–450 g were decapitated and their cerebella were immediately homogenized in 50 volumes (wt/vol) of ice cold buffer using a polytron at a setting of 5 for 30 seconds. The homogenate was centrifuged at $45000 \times g$ for 10 minutes at 4° C. The pellet was resuspended in 50 volumes of ice cold buffer and again centrifuged at $45000 \times g$ for 10 minutes at 4° C. The pellet was resuspended in 25 volumes of ice cold buffer with a polytron setting of 5 for 30 seconds.

III. Amitriptyline (non-radioactive binder) standard: A $10^{-3}$ M solution of amitriptyline in buffer was prepared. The solution was diluted into pooled normal human serum to obtain the following standards:

A. $10^{-4}$ M amitriptyline in serum
B. Serum with no added amitriptyline
C. $5 \times 10^{-6}$ M amitriptyline in serum
D. $1 \times 10^{-6}$ M amitriptyline in serum
E. $2 \times 10^{-7}$ M amitriptyline in serum
F. $4 \times 10^{-8}$ M amitriptyline in serum As used herein human serum and serum means human blood serum.

IV. Labeled ligand (radioactive binder): [$^3H$] mepyramine (pyrilamine, [pyridinyl-5-$^3H$]) (28.5 Ci/mmol) was obtained from New England Nuclear.

V. Samples: Patient's serum or amitriptyline dissolved in pooled normal serum were used as samples.

VI. Assay procedure: The assay is performed in $12 \times 75$ mm glass tubes. Unless specifically indicated all operations are performed at room temperature. Twenty microliters of standard or sample is added to each tube followed by 20 $\mu l$ of [$^3H$] mepyramine (~50,000 cpm per 20 $\mu l$) followed by 0.5 ml of cerebellar membranes. The contents of the tubes are mixed with a vortex mixer and incubated for 30 minutes. The tubes are then placed in an ice bath. 4 ml of ice cold buffer are added to each tube and the contents rapidly filtered with suction on Whatman GF/B glass fiber filters. The filters are rapidly washed with two 5 ml portions of ice cold buffer, and the vacuum dried filters placed in a scintillation vial containing 15 ml of Aquasol. After 18 hours the filters are counted in a liquid scintillation counter with a tritium window setting (Packard Spectrometer).

Figure 1:
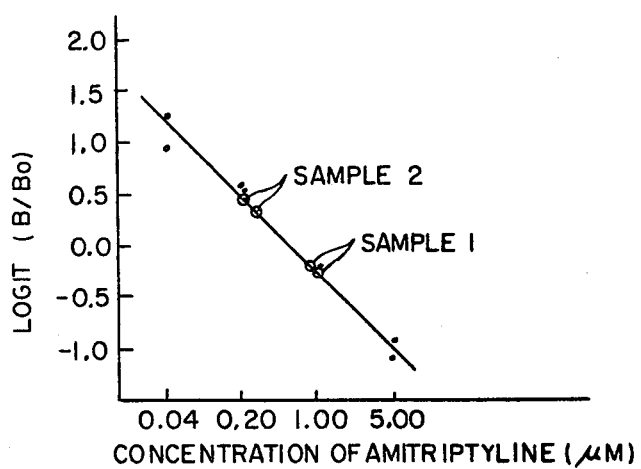
FIG. 1 is a graph showing logit (B/Bo) vs. amitriptyline in molar concentration reported in Example I and Table I.

Results: The results are calculated using a log-logit method as described in Rodbard, Clin. Chem. 20,1255–1270, 1974. The average cpm obtained with standard A is used to calculate the Background. Sample results and calculations are shown in Table I, and are plotted in FIG. 1.

TABLE I

Standard Curve:

| Tube No. | Standard | CPM | B/Bo | Logit | Conc. (μM) |
|---|---|---|---|---|---|
| 1 | A | 1187 | | | 100 |
| 2 | A | 1083 | | | 100 |
| 3 | A | 1484 | | | 100 |
| 4 | B | 9008 | | | 0 |
| 5 | B | 9554 | | | 0 |
| 6 | B | 9027 | | | 0 |
| 7 | C | 2132 | .111 | −0.904 | 5 |
| 8 | C | 1864 | 0.077 | −1.078 | 5 |
| 9 | D | 4383 | 0.394 | −0.187 | 1 |
| 10 | D | 4244 | 0.377 | −0.219 | 1 |
| 11 | E | 7523 | 0.789 | 0.574 | .2 |
| 12 | E | 7456 | 0.781 | 0.552 | .2 |
| 13 | F | 8804 | 0.951 | 1.284 | .04 |
| 14 | F | 8448 | 0.906 | 0.983 | .04 |

Background = 1251  Bo = 7945  Total CPM added = 44865

Samples

| Tube No. | Sample | CPM | B/Bo | Logit | Calculated conc. (μM) |
|---|---|---|---|---|---|
| 15 | *sample 1 | 4179 | 0.369 | −0.234 | 1.058 |
| 16 | *sample 1 | 4536 | 0.414 | −0.151 | 0.884 |
| 17 | +sample 2 | 6758 | 0.693 | 0.354 | 0.292 |
| 18 | +sample 2 | 7262 | 0.757 | 0.493 | 0.215 |

*Actual concentration in Sample 1 was 1 μM
+Actual concentration in Sample 2 was 0.2 μM

EXAMPLE II

Example II illustrates the measurement of blood serum antidepressant levels using a muscarinic cholinergic radioreceptor assay.

Materials and Methods

I. Muscarinic cholinergic receptor material: Male Sprague-Dawley weighing 100 g–150 g were decapitated. Their cerebella were removed and the remainder of their brains homogenized with a motor drive glass teflon homogenizer in 10 volumes (wt/vol) of ice cold 0.32 M sucrose. The homogenate was centrifuged at 1,000×g for 10 minutes at 4° C. The pellet was discarded and the supernatant was homogenized with a polytron (No. 5 setting, 30 seconds).

II. Standards: Amitriptyline (non-radioactive binder) standard was used for the measurement of serum amitriptyline levels. A $10^{-3}$ M solution of amitriptyline in 50 mM NaPO$_4$, pH 7.4 was prepared and diluted in the phosphate buffer to obtain the following standards.

A. $10^{-5}$ M amitriptyline
B. Phosphate buffer
C. $10^{-6}$ M amitriptyline
D. $2\times10^{-7}$ M amitriptyline
E. $4\times10^{-8}$ M amitriptyline
F. $8\times10^{-9}$ M amitriptyline Imipramine standards were used to measure serum concentrations of imipramine. A $10^{-2}$ M solution of imipramine in dimethylsulfoxide was diluted in the phosphate buffer to give the following standards:

A. $10^{-5}$ M amitriptyline
B. Buffer
C. $10^{-5}$ M imipramine
D. $2\times10^{-6}$ M imipramine
E. $4\times10^{-7}$ M imipramine As used herein serum means human blood serum.

III. Labeled Ligand (radioactive binder): [$^3$H] QNB, (Quinuclidinyl benzilate, DL-[benzilic-4,4'-$^3$H(N)], (28 Ci/mMol), was obtained from New England Nuclear and diluted to about 20,000 cpm with the sodium phosphate buffer.

IV. Samples: Patient's serum or amitriptyline or imipramine diluted into normal pooled human serum was used as samples.

V. Assay procedure: The assay is performed in 12×75 mm glass tubes. All procedures were performed at room temperature unless specifically indicated. One milliliter of [$^3$H] QNB was added to each tube. One hundred microliters of standard or of sample was added followed by 50 μl of receptor. The tubes were mixed with a vortex mixer. After 1 hour, 3 ml of ice cold sodium phosphate buffer, 50 mM, pH 7.4 was added to each tube and the contents rapidly filtered with vacuum over Whatman GF/B glass fiber filters. The filters were washed twice with 5 ml of ice cold buffer, and then placed in scintillation vials containing 15 ml of Aquasol. After 18 hours they were counted in a liquid scintillation counter with a tritium setting.

Figure 2:
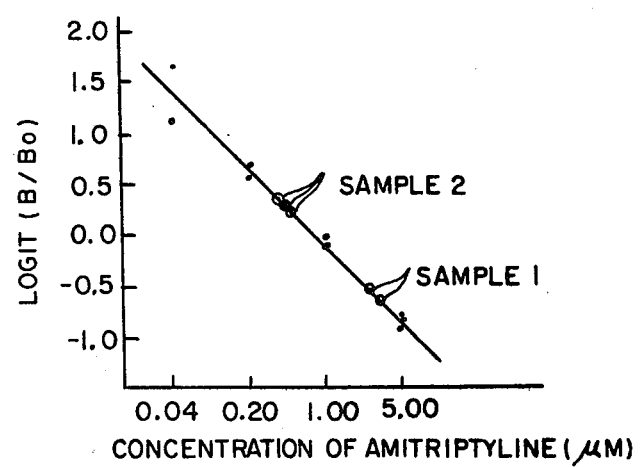
FIG. 2 is a graph showing logit (B/Bo) vs. amitriptyline in molar concentration reported in Example II and Table II.
Figure 3:
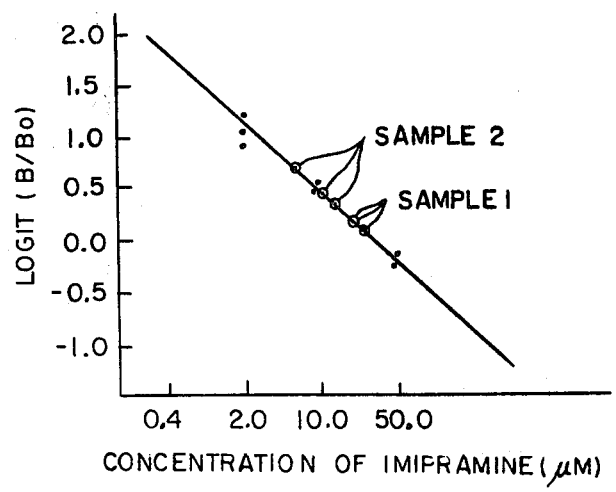
FIG. 3 is a graph showing logit (B/Bo) vs. imipramine in molar concentration reported in Example II and Table III.

Results: The results are calculated using a log-logit method as described in Rodbard, Clin. Chem. 20,1255–1270, 1974. The average cpm for standard A is used to calculate the background. Sample results for amitriptyline are calculated in Table II, and are plotted in FIG. 2. Sample results for imipramine are calculated in Table III, and are plotted in FIG. 3.

TABLE II

Amitriptyline standard curve.

| Tube No. | Standard | CPM | B/Bo | Logit | Conc. (μM) |
|---|---|---|---|---|---|
| 1 | A | 533 | | | |
| 2 | A | 529 | | | |
| 3 | A | 479 | | | |
| 4 | B | 10940 | | | |
| 5 | B | 11810 | | | |
| 6 | B | 11627 | | | |
| 7 | C | 1914 | .128 | −0.834 | 5.0 |
| 8 | C | 1790 | .117 | −0.879 | 5.0 |
| 9 | C | 1679 | .106 | −0.924 | 5.0 |
| 10 | D | 5285 | .436 | −0.112 | 1.0 |
| 11 | D | 5442 | .450 | −0.087 | 1.0 |
| 12 | D | 5239 | .432 | −0.119 | 1.0 |
| 13 | E | 9240 | .797 | 0.595 | 0.2 |
| 14 | E | 9692 | .839 | 0.716 | 0.2 |
| 15 | F | 11235 | .980 | 1.680 | 0.04 |
| 16 | F | 10780 | .938 | 1.180 | 0.04 |

BKG = 514  Bo = 10945

Samples:

| Tube No. | Standard | CPM | B/Bo | Logit | Calculated Conc. (μM) |
|---|---|---|---|---|---|
| 17 | Sample 1 | 2537 | .185 | −0.644 | 3.102 |
| 18 | Sample 1 | 2867 | .215 | −0.562 | 2.606 |
| 19 | Sample 2 | 7735 | .660 | 0.288 | 0.428 |
| 20 | Sample 2 | 7778 | .664 | 0.295 | 0.421 |
| 21 | Sample 2 | 7386 | .628 | 0.227 | 0.486 |

TABLE III

Imipramine Standard Curve

| Tube No. | Standard | CPM | B/Bo | Logit | Conc. (μM) |
|---|---|---|---|---|---|
| 1 | A | 533 | | | |
| 2 | A | 529 | | | |
| 3 | A | 479 | | | |
| 4 | B | 10940 | | | |
| 5 | B | 11810 | | | |
| 6 | B | 11627 | | | |
| 7 | C | 4922 | .403 | −0.171 | 50 |
| 8 | C | 4908 | .401 | −0.173 | 50 |
| 9 | C | 4803 | .392 | −0.191 | 50 |
| 10 | D | 8706 | .748 | 0.473 | 10 |
| 11 | D | 8704 | .748 | 0.473 | 10 |
| 12 | D | 8799 | .757 | 0.493 | 10 |
| 13 | E | 10370 | .901 | 0.957 | 2 |
| 14 | E | 10617 | .923 | 1.079 | 2 |
| 15 | E | 10843 | .944 | 1.224 | 2 |

BKG = 514  Bo = 10945

Samples:

| Tube No. | Sample | CPM | B/Bo | Logit | Calculated Conc. (μM) |
|---|---|---|---|---|---|
| 16 | Sample 1 | 7105 | .602 | 0.180 | 20.4 |
| 17 | Sample 1 | 7146 | .606 | 0.187 | 20.1 |
| 18 | Sample 1 | 6773 | .572 | 0.125 | 23.4 |
| 19 | Sample 2 | 9642 | .834 | 0.701 | 5.5 |
| 20 | Sample 2 | 8636 | .742 | 0.459 | 10.1 |
| 21 | Sample 2 | 8069 | .690 | 0.348 | 13.4 |

I claim:

1. The method of determining the concentration of tricyclic antidepressant drugs and any active metabolites thereof in a body fluid containing same comprising the independent procedures of (a) mixing together muscarinic cholinergic receptor material, radioactive muscarinic cholinergic receptor binder and body fluid, and measuring the amount of the radioactive muscarinic cholinergic binder on the muscarinic cholinergic receptor material and (b) mixing together a concentration of a standard amount of non-radioactive muscarinic cholinergic receptor binder, muscarinic cholinergic receptor material and radioactive muscarinic cholinergic receptor binder and measuring the amount of radioactive muscarinic cholinergic receptor binder on the muscarinic cholinergic receptor material.

2. The method of claim 1 in which the material, binder, and body fluid are permitted to remain together a time sufficient to produce sufficient binding of the binder, drugs and any active metabolites thereof in the body fluid to said receptor material prior to making the measurement.

3. The method of claim 1 in which the material, binder and body fluid are combined in the presence of sufficient buffer to produce a pH of about 6 to 9.

4. The method of claim 1 in which unbound binder and body fluid are removed as part of the measurement.

5. The method of claim 1, 2, 3 or 4 in which the body fluid is blood plasma or blood serum.

6. The method of claim 1 in which measuring of the amount of radioactive receptor binder on the receptor material is determined in a gamma detector or scintillation counter based upon the nature of the radionuclide portion of the radioactive binder.

7. The method of claim 1 or 6 in which the concentration of drug and active metabolite is determined by reference to a standard curve representing percent inhibition of radioactive receptor binder vs. non-radioactive receptor binder.

8. The method of claim 1 in which the concentration of body fluid is less than about 10%.

9. The method of claim 1 or 8 in which the body fluid is blood plasma or blood serum.

10. The method of claim 1, in which the amount of body fluid in the mixture containing same is greater than one microliter.

11. The method of claim 1 in which the unbound drug, unbound radioactive binder and body fluid are removed in determining the percent inhibition of binding.

12. The method of claim 1 in which the radioactive receptor binder is selected from the group consisting of radioactive labeled quinuclidinyl benzilate and radioactive labelled propylbenzilyl choline mustard.

13. The method of claim 1 in which the receptor material is brain tissue.

14. The method of claim 1 in which (b) is repeated a sufficient number of times while varying concentration of the non-radioactive binder to provide information for generating a standard curve.

15. As a mercantile unit, a kit of at least one container of radioactive muscarinic cholinergic binder, muscarinic cholinergic receptor material, and standard non-radioactive muscarinic cholinergic binder.

16. The kit of claim 15 in which the radioactive binder is selected from the group consisting of quinuclidinyl benzilate and propylbenzilyl choline mustard.

17. The kit of claim 15 or 16 in which the radioactive label is $^3H$, $^{125}I$ or $^{131}I$.

18. The method of determining the concentration of tricyclic antidepressant drugs and any active metabolites thereof in a body fluid containing same comprising the independent procedures of (a) mixing together histamine $H_1$ receptor material, radioactive histamine $H_1$ receptor binder and body fluid, and measuring the amount of the radioactive binder on the histamine $H_1$ receptor material and (b) mixing together a concentration of a standard amount of non-radioactive histamine $H_1$ receptor binder, histamine $H_1$ receptor material and radioactive histamine $H_1$ receptor binder and measuring the amount of radioactive histamine $H_1$ receptor binder on the histamine $H_1$ receptor material.

19. The method of claim 18 in which the material, binder, and body fluid are permitted to remain together a time sufficient to produce sufficient binding of the binder, drugs and any active metabolites thereof in the body fluid to said receptor material prior to making the measurement.

20. The method of claim 19 in which the material, binder and body fluid are combined in the presence of sufficient buffer to produce a pH of about 6 to 9.

21. The method of claim 18 in which unbound binder and body fluid are removed as part of the measurement.

22. The method of claim 18, 19, 20 or 21 in which the body fluid is blood plasma or blood serum.

23. The method of claim 18 in which the percent inhibition measuring of the amount of radioactive receptor binder on the receptor material is determined in a gamma detector or scintillation counter based upon the nature of the radionuclide portion of the radioactive binder.

24. The method of claim 18 or 23 in which the concentration of drug and active metabolite is determined by reference to a standard curve representing percent inhibition of radioactive receptor binder vs. drug non-radioactive receptor binder.

25. The method of claim 18 in which the concentration of body fluid is less than about 10%.

26. The method of claim 18 or 25 in which the body fluid is blood plasma or blood serum.

27. The method of claim 18, in which the amount of body fluid in the mixture containing same is greater than about one microliter.

28. The method of claim 18 or 25 in which the unbound drug, unbound radioactive binder and body fluid are removed in determining the percent inhibition of binding.

29. The method of claim 18 in which the radioactive receptor binder is radioactive labeled mepyramine.

30. The method of claim 18 in which the receptor material is brain tissue.

31. The method of claim 18 in which (b) is repeated a sufficient number of times while varying concentration of the non-radioactive binder to provide information for generating a standard curve.

32. As a mercantile unit, a kit of at least one container of radioactive histamine $H_1$ binder, histamine $H_1$ receptor material, and standard nonradioactive histamine $H_1$ binder.

33. The kit of claim 32 in which the radioactive binder is radioactive labeled mepyramine.

34. The kit of claim 32 or 33 in which the radioactive label is $^3H$, $^{125}I$ or $^{131}I$.

* * * * *